United States Patent [19]

Vasile

[11] 4,127,035
[45] Nov. 28, 1978

[54] ELECTROMAGNETIC TRANSDUCER

[75] Inventor: Carmine F. Vasile, Newbury Park, Calif.

[73] Assignee: Rockwell International Corporation, El Segundo, Calif.

[21] Appl. No.: 830,269

[22] Filed: Sep. 2, 1977

[51] Int. Cl.$^2$ ............................................. G01N 29/04
[52] U.S. Cl. .......................................... 73/629; 73/643
[58] Field of Search ................. 73/643, 627, 629, 600; 324/226, 227, 232, 234–238; 310/15

[56] References Cited

U.S. PATENT DOCUMENTS

| 3,583,213 | 6/1971 | Houck | 73/600 |
| 3,850,028 | 11/1974 | Thompson et al. | 73/643 |

FOREIGN PATENT DOCUMENTS

| 241,805 | 8/1969 | U.S.S.R. | 73/643 |
| 376,127 | 5/1973 | U.S.S.R. | 73/643 |

Primary Examiner—Richard C. Queisser
Assistant Examiner—John P. Beauchamp
Attorney, Agent, or Firm—L. Lee Humphries; Craig O. Malin

[57] ABSTRACT

A magnet is used to create a static magnetic field adjacent to the surface of a conductive material. At least one conductor runs through the magnetic field. When a pulse of current flows through the conductor, an elastic wave is generated in the material. In a preferred embodiment, a row of individual permanent magnets is used to create a periodic magnetic field. One side of a coil is placed in the periodic magnetic field so that a sheet of current moves transverse to the magnetic field when a pulse of current flows through the coil. When the coil is oriented parallel to the row of magnets, a horizontal shear wave is generated in the material. When the coil is oriented transverse to the row of magnets, a Lamb wave is generated in the material.

14 Claims, 5 Drawing Figures

ELECTROMAGNETIC TRANSDUCER

BACKGROUND OF THE INVENTION

A. Field of the Invention

This invention relates to the field of nondestructive inspection and particularly to the field of transducers for use in ultrasonic inspection.

B. Description of the Prior Art

Elastic or ultrasonic waves are commonly used to inspect parts for cracks and other defects. Generally, a narrow beam of a longitudinal or a transverse type wave is injected into the part by a transducer which directly contacts the part or indirectly contacts the part through a transmitting medium such as water which contacts both the transducer and the part being tested. A piezoelectric crystal in the transducer is used to generate the elastic wave.

More recently, non-contact type transducers have been developed which can generate elastic Lamb-type waves in an object of conductive material without any physical contact with the object. Non-contact transducers are particularly useful in applications where the transducer moves relative to the test object because it eliminates friction and wear of the transducer. One such non-contact transducer is the electromagnetic transducer described in U.S. Pat. No. 3,850,028. Such prior art non-contact transducer utilizes a meander coil placed within a static magnetic field to generate Lamb waves by means of a Lorentz force mechanism.

The prior art meander coil electromagnetic transducer can generate only a Lamb type wave which fills the entire cross-section of the part. While Lamb waves can be advantageously used for inspecting parts such as large diameter pipelines (see for example, patent application No. 731,199), they have low radiation impedance and consequently require strong magnetic fields and high currents to obtain strong signals. For applications involving a small confined space, such as the inspection of tubes from the inside, it is difficult to provide the strong magnetic fields and high currents required to obtain strong signals using Lamb waves generated by meander coil transducers.

SUMMARY OF THE INVENTION

It is an object of the invention to provide an improved noncontact transducer.

It is an object of the invention to provide non-contact transducers which can generate horizontal shear waves or Lamb waves.

It is an object of the invention to provide an electromagnetic transducer for generating torsional waves in tubes and cylinders.

It is an object of the invention to provide an electromagnetic transducer having good efficiency at low frequencies.

It is an object of the invention to provide a non-contact transducer whose efficiency can be increased without restricting its acoustic bandwidth.

It is an object of the invention to provide a non-contact transducer which can be placed inside a tube to inspect the tube by transmitting and receiving elastic waves in the wall of the tube.

According to the invention, a magnet is used to create a static magnetic field adjacent to the surface of a conductive material. At least one conductor runs through the magnetic field. When a pulse of current flows through the conductor, an elastic wave is generated in the material. In a preferred embodiment, a row of individual permanent magnets is used to create a periodic magnetic field. One side of a coil is placed in the periodic magnetic field so that a sheet of current moves transverse to the magnetic field when a pulse of current flows through the coil. When the coil is oriented parallel to the row of magnets, a horizontal shear wave is generated in the material. When the coil is oriented transverse to the row of magnets, a Lamb wave is generated in the material.

Unlike prior art electromagnetic transducers, periodicity in the magnetic field is obtained by the design of the static magnetic field rather than by the use of a meander type coil to create periodicity in the alternating magnetic field created by the current flow. Further, at any given time, current in the coil exposed to the static magnetic field flows in the same direction rather than in opposing directions as in conventional coils.

The transducer operates in a reciprocal manner as a receiver, generating electrical signals as elastic waves pass underneath it.

These and other objects and features of the present invention will be apparent from the following detailed description, taken with reference to the accompanying drawings.

DESCRIPTION OF THE PREFERRED EMBODIMENT

Figure 1:
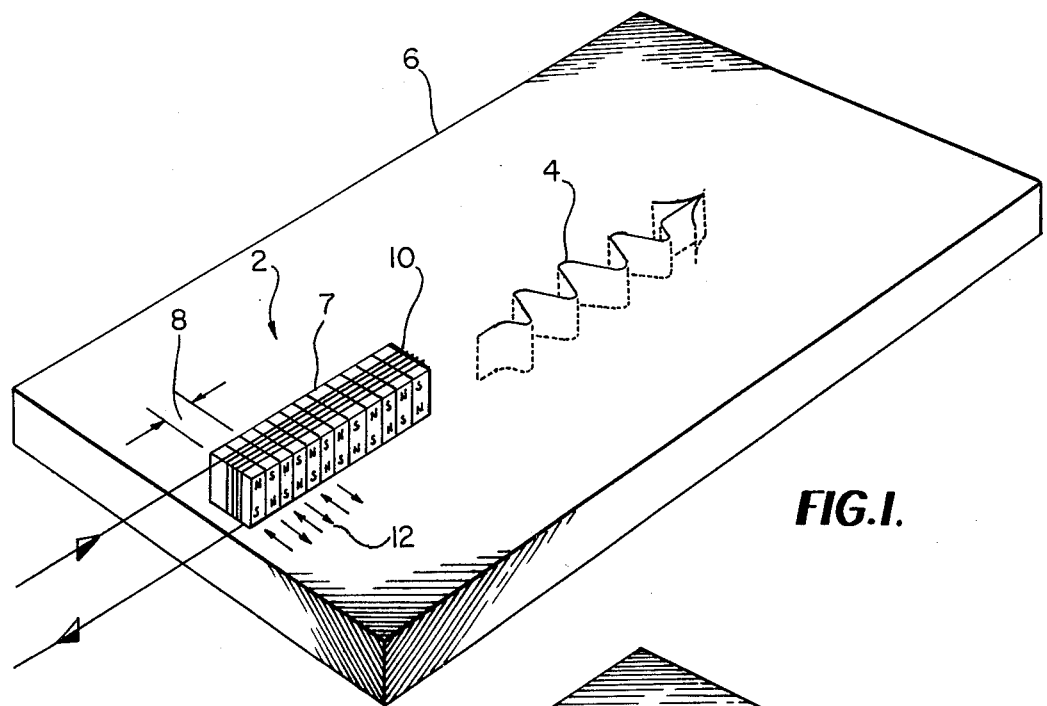
FIG. 1 is a perspective view of a transducer producing horizontal shear waves in a test plate.

FIG. 1 shows a transducer 2 for generating (or receiving) horizontal shear waves 4 in an object of conductive material such as metal test plate 6. Transducer 2 comprises a plurality of permanent magnets 7 abutting each other to form a row. Adjacent magnets in the row have opposite polarity, thus creating a periodic, static magnetic field adjacent to and in plate 6. The period 8 of the static magnetic field is equal to the thickness of two abutting magnets.

A coil 10 is wrapped around the complete row of magnets in the longitudinal direction so that a pulse of current can flow in the same direction in all the wires between magnets 7 and plate 6. Thus, according to the known Lorentz force mechanism, when a current flows in the wires of coil 10 between magnets 7 and plate 6, an eddy current is induced in test plate 6 and this eddy current interacts with the static magnetic field to produce horizontal shear forces 12 that launch ultrasonic waves 4 down plate 6.

Figure 2:
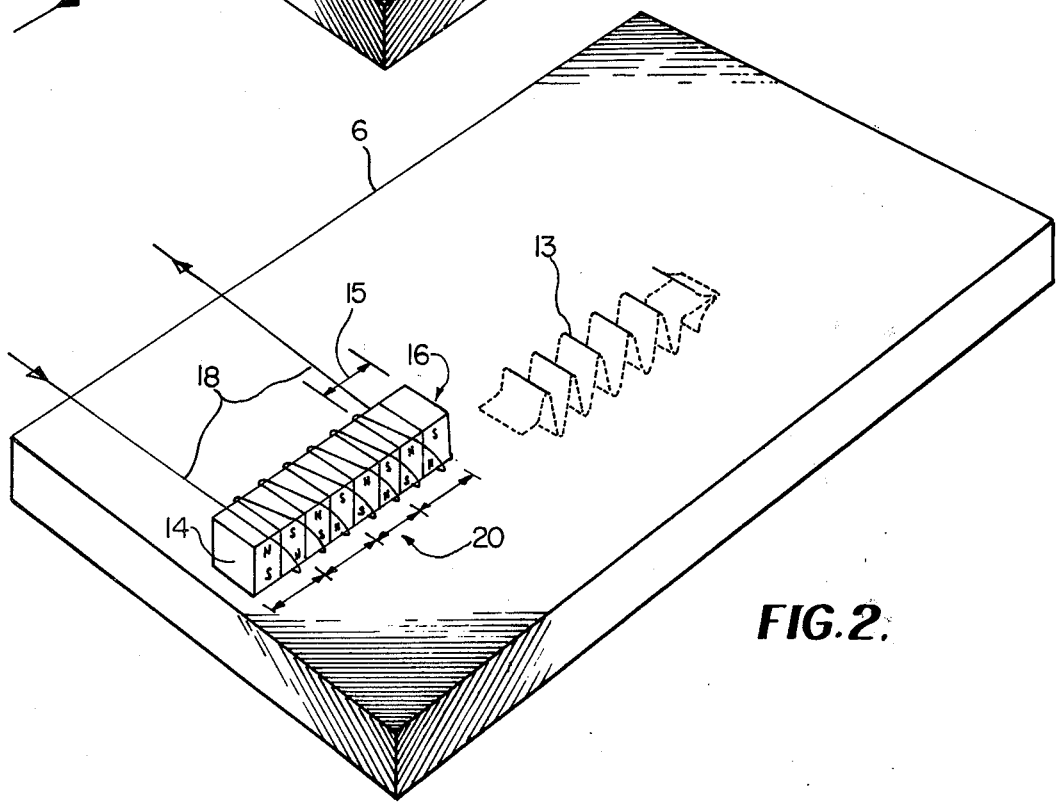
FIG. 2 is a perspective view of a transducer producing Lamb waves in a test plate.

FIG. 2 shows a second embodiment of the invention used to generate (or receive) Lamb waves 13 (rather than the previously mentioned horizontal shear waves 4) in a test object 6. A plurality of permanent magnets 14 are stacked to form a row of magnets having alternating polarity and period 15 in the same manner as described for horizontal shear wave transducers 2. However, in Lamb wave transducer 16, coil 18 is wound so that the wires run transverse to the length of the periodic, static magnetic field created by the row of magnets.

Thus, when a signal is supplied to coil 18, a sheet of current flows in one direction in the periodic, static magnetic field adjacent metal plate 6. Such current induces an eddy current in plate 6 and this eddy current interacts with the static magnetic field to produce forces 20 which launch Lamb waves 13 down plate 6.

Figure 3:
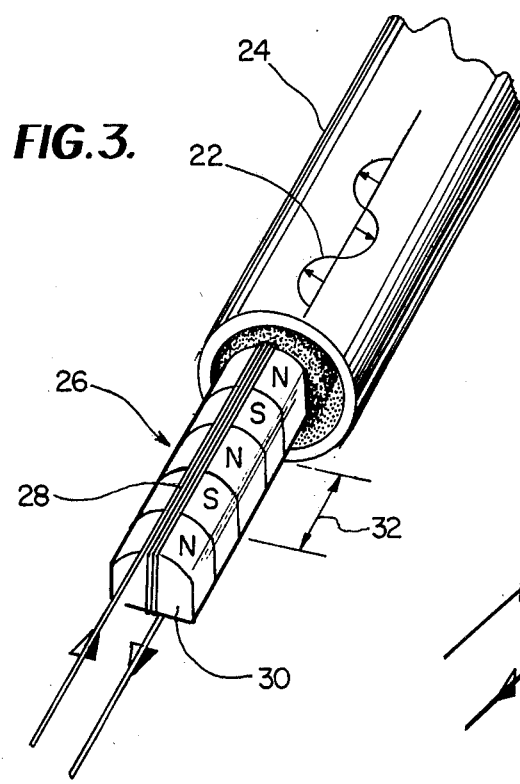
FIG. 3 is a perspective view of a transducer producing torsional waves in a tube.

FIG. 3 schematically shows a third embodiment of the invention used to generate torsional wave 22 in metal tube 24. Torsional wave 22 is basically a shear wave created in a cylindrical object and therefore torsional wave transducer 26 is wound similarly to shear transducer 2. Coil 28 extends along the length of the row of permanent magnets 30 and when current flows in coil 28 horizontal shear forces are created as shown by the arrows forming torsional wave 22. This wave will have a wavelength related to period 32. As shown in FIG. 3, the surface of magnets 30 that are used to establish the periodic magnetic field in tube 24 are curved to match the inside surface of the tube.

A transmitting transducer which was constructed to inspect 7/8 inch diameter tubes having a wall thickness of 0.050 inch utilizes twelve samarium cobalt permanent magnets 30 capable of producing a periodic 2.4 KG normal field. The magnets have a seven-sixteenths inch radius and about 0.32 inch of arc length. Their thickness is 0.125 inch so that the period 32 of the field is 0.25 inch. Coil 28 consists of 24 turns of #36 bifilar wire. A spring clip attached to the transducer allows it to pass through dented regions in the tube.

A receiving transducer also used to inspect the seven-eigths inch diameter tubes is similar to the transmitting transducer except that only six magnets are used and the coil has 48 turns. The transmitter series resonant input impedance is approximately 8Ω with a Q of 3.3 at 0.5 MHz. The receiver also has a Q of 3.3 with a parallel resistance of approximately 230Ω at 0.5 MHz.

Figure 4:
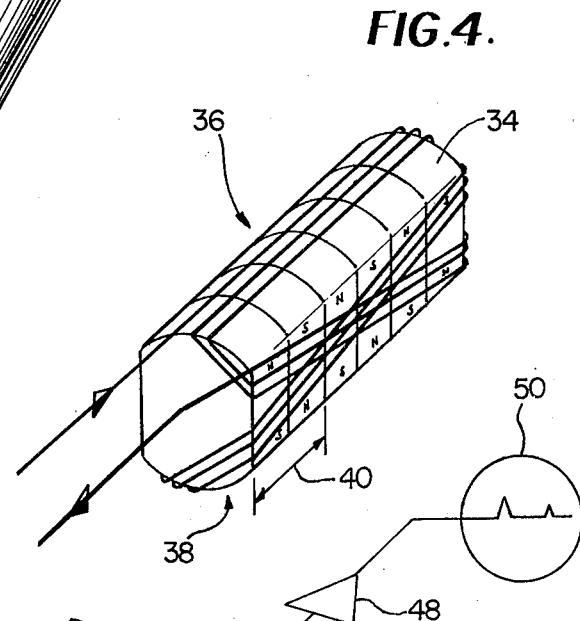
FIG. 4 is a perspective view of a transducer wound to produce torsional waves on both sides of a tube.

FIG. 4 shows a variation of a transducer for producing torsional waves in a tube. The magnets 34 in this transducer are curved on opposite sides to be concentric with diametrically opposite surfaces on the inside of the tube being inspected. The coil is wound so that the direction of the current is the same in the conductors on the upper surface 36 as it is on the lower surface 38. This transducer generates (or receives) a torsional wave having a period 40 from both the upper and lower surfaces. Consequently, the circumferential torsional wave generated by the transducer of FIG. 4 is twice as strong as the circumferential torsional wave generated by the one-sided transducer of FIG. 3.

The double-sided transducer of FIG. 4 can be wrapped with a coil in the manner shown in FIG. 1 so that current flows in opposite directions on diametrically opposed surfaces 36, 38. Such a transducer can excite the higher order circumferential torsional waves, but will not excite the lowest order circumferential wave. The transducers shown in FIGS. 3 and 4 can excite both the higher order circumferential waves and the lowest order wave.

A single conductor passing under the field created by either a single magnet or a periodic magnet can create an elastic wave in an adjacent conductive material according to the principles of the invention. However, the efficiency of a single conductor transducer is low because the efficiency of the transducer depends directly upon the number of conductors (turns in the coil) passing through the field.

Likewise, a single magnet can be used in conjunction with a conductor to create an elastic wave in a conductive material. However, the wave launched will not have a particular frequency and can't be separated from other elastic waves. Therefore, it is preferred to use a static, periodic magnet field, as described above, and utilize an RF signal to drive the coil. For example, for thick metal plates the frequency of the RF signal used is matched to the periodicity of the static field according to the formula:

$$D = (v_s/f \sin \theta), \qquad (1)$$

wherein: $D$ = the thickness of two adjacent magnets (8, 20, 32, and 40 of FIGS. 1-4),
$v_s$ = the velocity of the shear wave in the material being tested,
$f$ = frequency of the RF signal, and
$\theta$ = the angle between the surface normal and the shear wave beam radiated into the material.

For thin plates, e.g. horizontally polarized plate modes, the periodicity of the static field is given by:

$$D = 1/\sqrt{(f/v_2)^2 - (n/2t)^2} \qquad (2)$$

where: $n$ = mode index 0, 1, 2, etc., $t$ = plate thickness

Similarly, for a transversely wound coil, FIG. 2, used with a thick plate, a shear wave having a vertical component of polarization (sv wave) as well as a longitudinal wave can be excited. In such case, the periodicity $D$ is given by equation (1) for the sv wave and by $$D = (v_1/f \sin \theta) \qquad (3)$$

for the longitudinal wave. In such case the relation for the Lamb wave in thin plates must be generated numerically according to known principles, see for example *Acoustic Fields and Waves in Solids* by B. A. Auld, (Wiley, 1973).

Increasing the quantity of adjacent magnets in the transducer increases the intensity or magnitude of the wave being generated and narrows its bandwidth.

Figure 5:
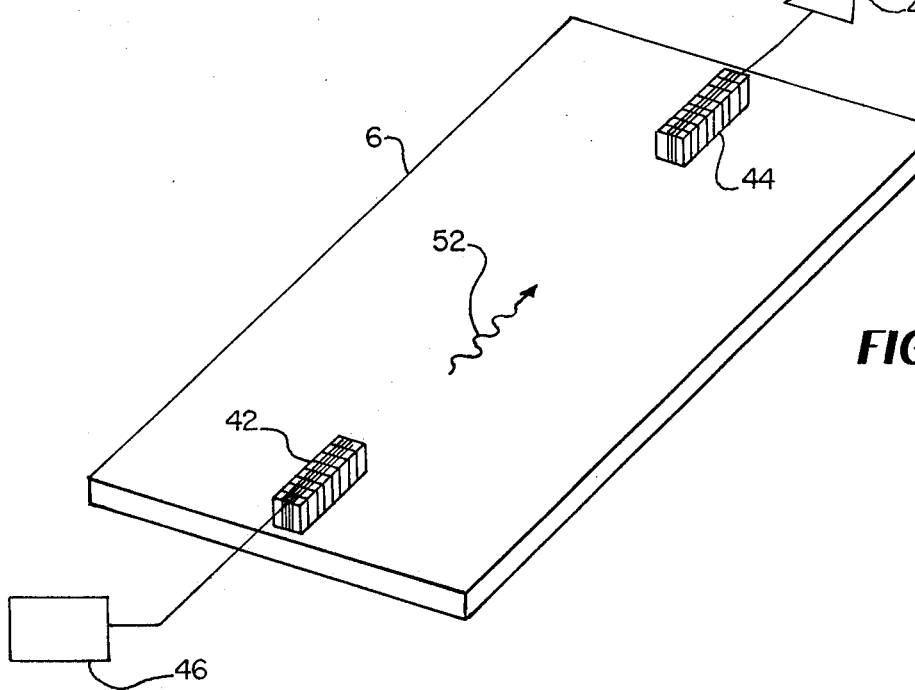
FIG. 5 is a schematic view of a transmitter and receiver being used to test a plate.

Means of generating, amplifying, and measuring RF waves are well known in the art of ultrasonic inspection. FIG. 5 shows a schematic arrangement of such known equipment for evaluating and using transducers 42, 44 according to the present invention. A transmitter 42 is placed on plate 6 and a receiver 44 is placed on the same plate 6 at a distance from the transmitter 42. A Matec RF pulse generator 46 is suitably power matched to the coil of transmitter 42. The frequency of the RF pulse generated by generator 46 is selected to match the period of the transmitter 42 and receiver 44 according to the previously mentioned formulas.

A low noise amplifier 48 is suitably matched to the coil of receiver 44 and an oscilloscope 50 is driven by amplifier 48. When a pulse of RF power is sent by generator 46 to the coils of transmitter 42, an ultrasonic wave 52 is created in plate 6, as previously described. This wave propagates through the material at a speed of $v_s$ according to known principles until it reaches receiver 44. At receiver 44, the wave creates electric signals in the receiver coil in a manner which is reciprocal to its generation. These signals are displayed in scope 50.

Of course, a single transducer can be used as both a transmitter and as a receiver to locate defects in a material by reflection of the transmitted wave from the defect. Similarly, the transducers of the present invention can be used in other inspection systems that are analogous to conventional ultrasonic inspection systems using prior art piezoelectric and electromagnetic transducers.

The static magnetic field can be created by means other than by the use of adjacent permanent magnets. For example, if every other magnet in the row is simply replaced by a non-magnetic material, a useable periodic magnetic field will be obtained from the spaced apart magnets of similarly oriented polarity. Or, a single horseshoe type magnet with a pole piece having a row of periodic projections between the poles of the magnet will create a periodic magnet field. In some applications, it may be advantageous to utilize electromagnets to provide the periodic magnetic field.

In certain applications, the part being tested can itself be used (rather than a separate coil) as the conductor for passing the RF signal through the magnetic field. Additionally, curved transducers which mate with the outside of a pipe or cylinder can be used. Further, the surface of the magnets can be metallized to minimize inductance between the coil and the magnets.

Numerous variations and modifications may be made without departing from the present invention. Accordingly, it should be clearly understood that the form of the present invention described above and shown in the accompanying drawings is illustrative only and is not intended to limit the scope of the present invention.

What is claimed is:

1. A transducer for generating an elastic wave in a conductive material, comprising:
    means for creating a periodic magnetic field adjacent to and in the conductive material; and
    means for conducting a current in substantially one direction, at a given time, through said periodic magnetic field, whereby an elastic wave is launched in the conductive material, said wave having a wavelength related to the period of said periodic magnetic field.

2. The transducer as claimed in claim 1, wherein said means for creating a period magnetic field comprises a row of permanent magnets, the N-S axes of said magnets being substantially parallel, and adjacent magnets in said row having differently oriented polarity.

3. The transducer as claimed in claim 1, wherein said means for creating a periodic magnetic field comprises a row of spaced apart permanent magnets, the N-S axes of said magnets being substantially parallel, and each magnet in said row having similarly oriented polarity.

4. The transducer as claimed in claim 1, wherein said means for creating a periodic magnetic field comprises a magnet with a pole piece having a row of periodic projections.

5. The transducer as claimed in claim 1, wherein said means for conducting a current comprises a coil having one of its sides in said periodic magnetic field adjacent the conductive material.

6. The transducer as claimed in claim 1, wherein said means for conducting a current comprises a coil, one side of said coil being positioned in said periodic magnetic field adjacent the conductive material so that current in said coil flows substantially parallel to said periodic magnetic field and perpendicular to the N-S axes of the individual fields forming said periodic magnetic field, whereby a horizontal shear wave is generated in said conductive material.

7. The transducer as claimed in claim 1, wherein said means for conducting a current comprises a coil, one side of said coil being positioned in said periodic magnetic field adjacent the conductive material so that current in said coil flows substantially transverse to both said periodic magnetic field and the N-S axes of the individual fields forming said periodic magnetic field, whereby a Lamb wave is generated in said conductive material when said material is thin and an sv wave is generated when said material is thick.

8. A transducer for generating a torsional elastic wave in a cylindrical object of conductive material, comprising:
    means for creating a periodic magnetic field along a portion of the length of the cylindrical object, the N-S axes of the individual magnetic fields forming said periodic magnetic field being perpendicular to the cylindrical object; and
    means for conducting a current in substantially one direction at a given time parallel to the cylindrical object and in said periodic magnetic field, whereby a torsional elastic wave is generated in the cylindrical object.

9. The transducer as claimed in claim 8, wherein the cylindrical object comprises a tube, and the transducer is placed inside the tube.

10. The transducer as claimed in claim 8, wherein said means for creating a periodic magnetic field creates periodic magnetic fields on diametrically opposite sides of the cylindrical object and wherein said means for conducting a current conducts said current through both said periodic magnetic fields.

11. The transducer as claimed in claim 10, wherein said means for conducting a current conducts said current through both said periodic magnetic fields in substantially the same direction at a given time, whereby both the lowest and higher order circumferential torsional waves are excited in the tube.

12. The transducer as claimed in claim 10, wherein said means for conducting a current conducts said current through one of said periodic magnetic field, in one direction and through the other of said periodic magnetic fields in the opposite direction at a given time, whereby only the higher order circumferential torsional waves are excited in the tube.

13. A method of generating elastic waves in conductive material, comprising:
    creating a periodic magnetic field in and adjacent to the conductive material; and
    conducting a sheet of current in substantially one direction through said magnetic field, whereby an elastic wave is generated in the conductive material.

14. A nondestructive method of testing conductive materials utilizing elastic waves comprising the steps of:
    creating a static, periodic magnetic field in and adjacent to the conductive material;
    passing an RF current in substantially one direction, at a given time, through said static, periodic magnetic field, the frequency of said RF current being selected to match the periodicity of said static, periodic magnetic field so that an elastic wave is generated in the conductive material; and
    detecting echoes of said elastic wave as it is reflected from discontinuities in the conductive material.

* * * * *